United States Patent
Gibbins

[19]

[11] Patent Number: 5,928,174
[45] Date of Patent: Jul. 27, 1999

[54] WOUND DRESSING DEVICE

[75] Inventor: Bruce L. Gibbins, Portland, Oreg.

[73] Assignee: Acrymed, Portland, Oreg.

[21] Appl. No.: 08/971,074

[22] Filed: Nov. 14, 1997

[51] Int. Cl.[6] ........................................... A61M 5/32
[52] U.S. Cl. ................................. 602/41; 602/43; 602/48
[58] Field of Search ..................................... 602/41, 43, 48

[56] References Cited

U.S. PATENT DOCUMENTS

| | | | |
|---|---|---|---|
| 3,157,524 | 11/1964 | Artandi | 106/122 |
| 3,645,835 | 2/1972 | Hodgson | 161/146 |
| 3,969,498 | 7/1976 | Catania et al. | 424/28 |
| 4,320,201 | 3/1982 | Berg et al. | 435/265 |
| 5,196,190 | 3/1993 | Nangia et al. | 424/78.06 |
| 5,660,854 | 8/1997 | Haynes et al. | 424/450 |
| 5,725,491 | 3/1998 | Tipton et al. | 602/43 |

FOREIGN PATENT DOCUMENTS 1471013   4/1977   United Kingdom .

Primary Examiner—Richard J. Apley
Assistant Examiner—Kelvin Hart
Attorney, Agent, or Firm—Jones & Askew, LLP

[57] ABSTRACT

Methods and devices for treating wounds are provided. The device is uniquely constructed of multiple strands that are bound together in a minimal area resulting in a device constructed predominantly of free floating, loose strands. The free floating, loose strands, make the device flexible, allowing it to easily conform to irregular contours of wound beds and cavities. In addition, the free floating strands maximize the surface area of the device thereby optimizing the absorption capacity. The device improves overall wound healing by uniquely regulating moisture control at the wound and wound dressing device interface. Wound healing is further enhanced by facilitation of autolytic debridement which occurs as a result of mechanical interaction between the free floating strands and the wound site.

13 Claims, 2 Drawing Sheets

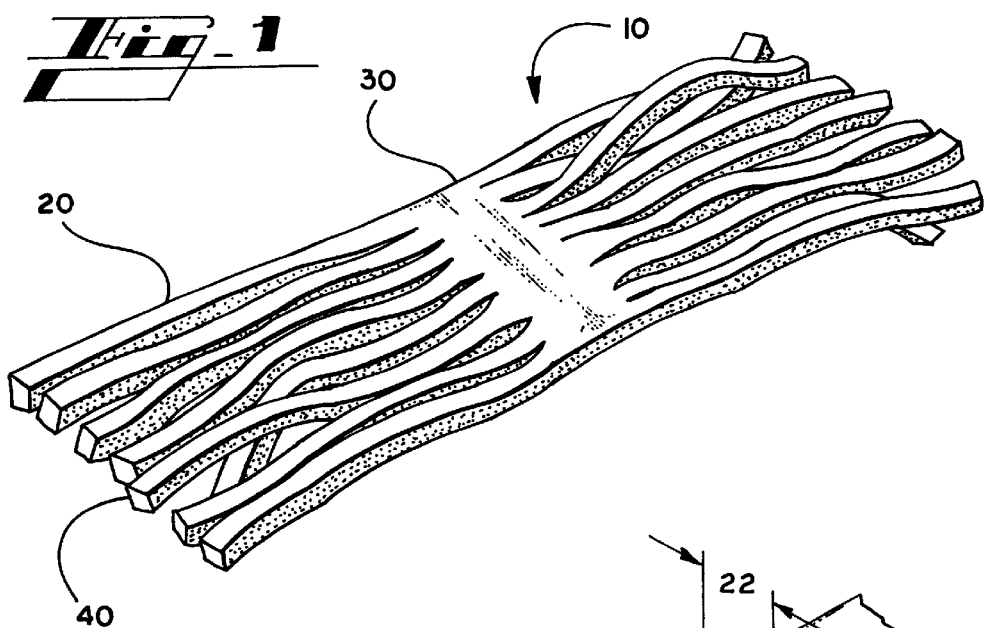
Fig_1
Fig_2
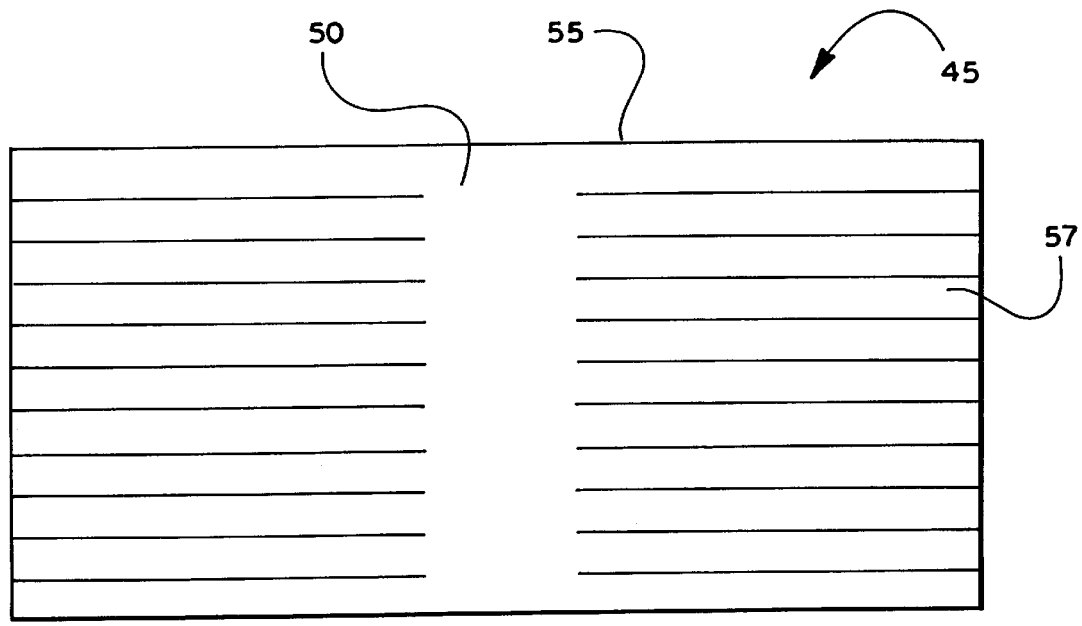
Fig_3

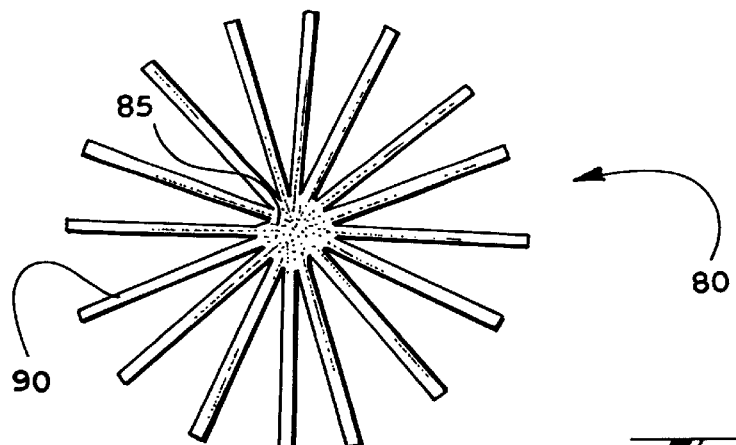
_Fig_ 4
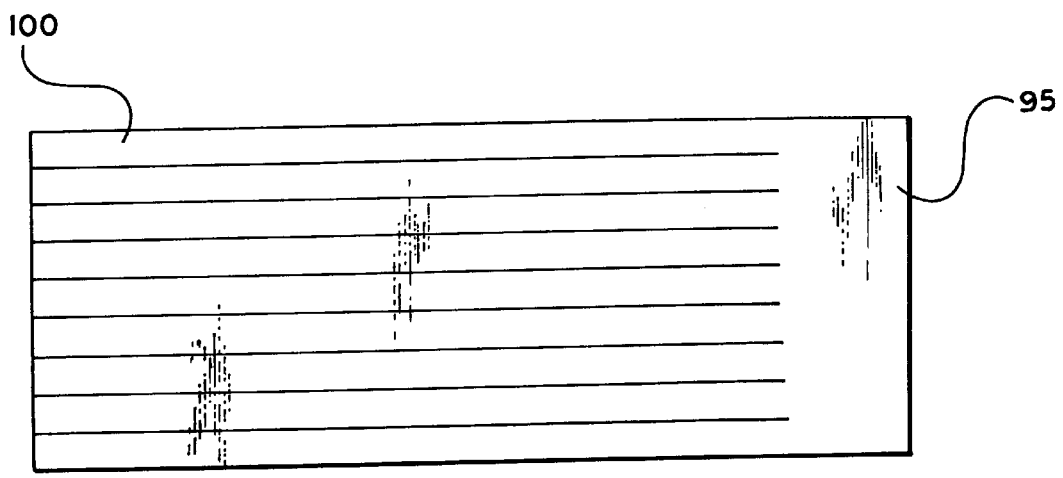
_Fig_ 5
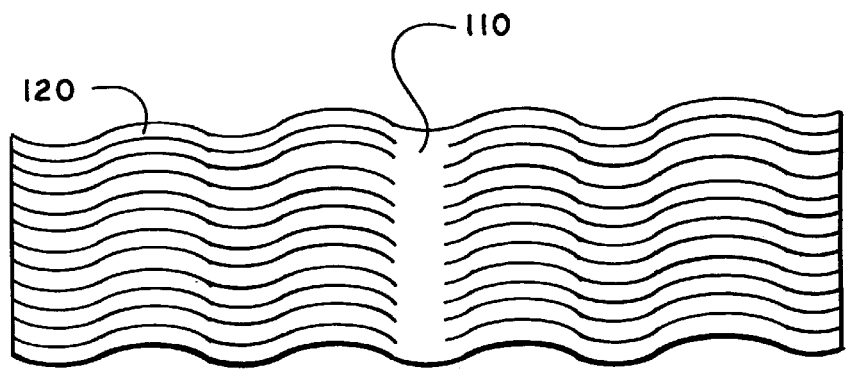
_Fig_ 6

WOUND DRESSING DEVICE

FIELD OF THE INVENTION

The present invention relates generally to the field of wound dressings and particularly to a novel device for draining deeply cavitated wounds. The wound dressing device possesses a high moisture absorption capacity, and is designed to regulate moisture at the wound bed-dressing interface. In addition the wound dressing facilitates and accelerates wound healing through autolytic debridement.

BACKGROUND OF THE INVENTION

The outer layer of skin surrounding the body performs an important protective function as a barrier against infection, and serves as a means of regulating the exchange of heat, fluid and gas between the body and external environment. When skin is removed or damaged by being abraded, burned or lacerated, this protective function is diminished. Areas of damaged skin are conventionally protected by the application of a wound dressing which facilitates wound healing by acting as a skin substitute.

Wounds to skin and the underlying tissues of animals may be caused by external insult such as friction, abrasion, laceration, burning or chemical irritation. Damage to such tissues may also result from internal metabolic or physical dysfunction, including but not limited to bone protrudence, diabetes, circulatory insufficiencies, or inflammatory processes. Normally tissue damage initiates physiological processes of regeneration and repair. In broad terms, this process is referred to as the wound healing process.

The wound healing process usually progresses through distinct stages leading to the eventual closure, and restoration of the natural function of the tissues. Injury to the skin initiates an immediate vascular response characterized by a transient period of vasoconstriction, followed by a more prolonged period of vasodilation. Blood components infiltrate the wound site, endothelial cells are released, exposing fibrillar collagen, and platelets attach to exposed sites. As platelets become activated, components are released which initiate events of the intrinsic coagulation pathway. At the same time, a complex series of events trigger the inflammatory pathways generating soluble mediators to direct subsequent stages of the healing process.

Normally, the wound healing process is uneventful and may occur regardless of any intervention, even in the case of acute or traumatic wounds. However, where an underlying metabolic condition or perpetual insult such as pressure is a contributing factor, the natural wound healing process may be retarded or completely arrested, resulting in a chronic wound. Trends in modern medical practices have shown that the wound healing of both acute and chronic wounds may be significantly improved by clinical intervention using methods and materials that optimize wound conditions to support the physiological processes of the progressive stages of wound healing. Key factors in providing the optimal conditions are the prevention of scab formation and the maintenance of an optimal level of moisture in the wound bed. Both of these factors can be controlled by the management of wound exudate fluid.

A common problem in the management of both acute and chronic wounds is the maintenance of an optimal level of moisture over the wound bed during heavy exudate drainage. This is usually, but not always, an early stage of healing. Most moist wound dressing technologies such as thin films, hydrocolloid dressings and hydrogels are typically overwhelmed by the accumulated exudate moisture during this heavy drainage phase. Management of moisture during heavy exudate drainage often necessitates the use of gauze or sponge packings that wick away excess moisture from the wound bed, thin film coverings that trap exudate fluid over the wound bed, or calcium alginate dressings that chemically bind exudate moisture due to the hydroscopic properties of the seaweed extract.

Examples of wound dressings that have been developed include collagen dressings. Soluble collagen has been used as a subcutaneous implant for repairing dermatological defects such as acne scars, glabellar furrows, excision scars and other soft tissue defects. Collagen has also been used in many forms as wound dressings such as collagen sponges, as described in Artandi, U.S. Pat. No. 3,157,524 and Berg et al, U.S. Pat. No. 4,320,201. However, most of these dressings are not satisfactory for the various types of full thickness wounds. Collagen films and sponges do not readily conform to varied wound shapes. Furthermore, some collagen wound dressings have poor fluid absorption properties and undesirably enhance the pooling of wound fluids.

Another example of wound dressings that have been developed are hydrocolloid dressings. UK Patent Number 1,471,013 and Catania et al., U.S. Pat. No. 3,969,498 describe hydrocolloid dressings that are plasma soluble, form an artificial eschar with the moist elements at the wound site, and gradually dissolve to release medicaments. These dressings comprise a hydrophilic foam of dextran polymer that can be applied without therapeutic agents or ointments, are non-irritating to the lesion and can be easily removed.

Known hydrocolloid dressings in general, and the Catania et al. dressings in particular, are subject to a number of drawbacks. The major disadvantages of these dressings include the potential to disintegrate in the presence of excess fluid at the wound site, and minimal (virtually negligible) control over water loss from the wound. This latter disadvantage is particularly important as excess water loss from a wound will cause an increase in heat loss from the body as a whole, potentially leading to hypermetabolism. In addition, hydrocolloid dressings require frequent dressing changes. This is especially true of the Catania et al. dressing due to the dissolution of the dextran polymer at the wound site caused by the fluid loss through the wound in the exudative stage.

Although currently available dressing materials possess features that contribute to the control of heavy exudate drainage, most also possess significant limitations that retard the overall healing process. For example, thin film dressings such as those described in U.S. Pat. No. 3,645,835, maintain excessive moisture over the wound bed, contributing to the overhydration (maceration) of surrounding skin. Although sponges and gauze support tissue, they require frequent changing, and cause irritation to the wound bed during body movement and dressing removal. Calcium alginates turn into a gelatinous mass during interaction with moisture, are difficult to remove completely, and often dehydrate the wound bed due to the hydroscopic nature of the matrix.

Importantly, none of the presently available devices significantly contribute to or support the autolytic debridement phase, which is the natural removal process of necrotic tissue and debris from the wound. Autolytic debridement is a key early stage event that precedes repair phases of healing. When wound conditions are not optimal for supporting autolytic debridement, then clinical procedures such as surgical removal, irrigation, scrubbing, and enzymatic or chemical methods must be used to remove the necrotic tissue and escar that can inhibit wound healing.

Temporary or permanent wound dressings that are designed to enhance wound healing are needed to cover large open wounds on patients with extensive burns, lacerations and skin damage. Furthermore the ability to produce wound dressings in a variety of shapes to accommodate multiple sizes and forms of injuries is important in the manufacture of useful medical products.

In addition, there continues to be a need for a wound dressing that possesses high moisture absorption capacity, a high rate of absorption, as well as a capacity to regulate moisture at the wound bed-dressing interface. Desirably, such a wound dressing device should stimulate the autolytic debridement process, especially during the heavy exudating phase of wound care management.

SUMMARY OF THE INVENTION

In accordance with the present invention, a novel wound dressing device having superior moisture absorption and regulation capacity is provided. The device is designed for use on heavily to moderately draining wounds and is made from a matrix suitable for application to broken skin and underlying tissues. The unique arrangement of the device allows it to both absorb excess wound exudate, and simultaneously conform closely to the walls of the wound bed, in order to accelerate overall wound healing.

The wound dressing device of the present invention is particularly desirable because the novel design provides a high surface area to volume ratio to maximize interchange between the matrix and wound moisture and wound debris. In addition the device is a single unit construction that is applied and removed as a complete unit, leaving no remnants and simplifying the overall wound dressing procedure. The device may also be left in place for prolonged periods between changes.

The free floating ends of the wound dressing increase the inherent flexibility of the device, and enhance conformability to the irregularities of the contours in the wound cavity. In addition, the free floating ends participate in mechanical debridement thereby accelerating the wound healing process. The multiple strands of the device provide maximal inter-strand space to serve as a reservoir for moisture, necrotic materials, or agents scheduled for delivery to the wound bed.

Accordingly, it is an object of the present invention to provide a wound dressing device that is particularly suited for use on deeply cavitated wounds.

Another object of the present invention is to provide a wound dressing device that will facilitate and accelerate the wound healing process.

An object of the present invention is to provide a wound dressing device that will absorb excess moisture at a wound site.

It is another object of the present invention to provide a wound dressing device that will facilitate and accelerate the wound healing process by promoting autolytic debridement.

Yet another object of the present invention is to provide a wound dressing device that will improve the wound healing process by absorbing extraneous exudate from the wound without dehydrating the wound.

Another object of the present invention is to provide a wound dressing device that will absorb wound exudate by allowing for optimal contact between the device and the wound area.

Yet another object of the present invention is to provide a wound dressing device that is suitable for external and internal wounds.

Another object of the present invention is to provide a wound dressing device that will enhance tissue repair and regeneration.

An object of the present invention is to prevent infection by providing a wound dressing device that will clean a wound site by removing debris and contaminating material.

It is another object of the present invention to provide a wound dressing device that will easily conform to the shape of a wound.

It is yet object of the present invention to provide a wound dressing device that is easy to manufacture.

Another object of the present invention is to provide a wound dressing device that may be easily removed and replaced.

Yet another object of the present invention is to provide a wound dressing device that is compatible with injured tissue and does not induce irritation or inflammation.

It is yet another object of the present invention is to provide a wound dressing device that can simultaneously function as a device to absorb wound exudate and promote autolytic debridement.

Another object of the present invention is to provide a method for making a single unit construction wound dressing device having multiple strands.

Yet another object of the present invention is to provide a method for treating wounds using a wound dressing device.

It is another object of the present invention to provide a method for treating wounds using a wound dressing device wherein the device may simultaneously absorb wound exudate, and deliver wound healing agents.

These and other objects, features and advantages of the present invention will become apparent after a review of the following detailed description of the disclosed embodiments and the appended claims.

BRIEF DESCRIPTION OF THE FIGURES

FIG. 1 is a three dimensional view of one embodiment the wound dressing device 10 of the present invention wherein 20 marks a strand of the multi-strand device with free floating strand ends 40.

FIG. 2 presents a cross-section 22 of a strand 20 of the multi-strand device 10.

FIG. 3 is an illustration of a pattern of a die used for cutting a device from an appropriate matrix material.

FIGS. 4–6 illustrate some patterns for alternative embodiments of the wound dressing.

DETAILED DESCRIPTION

An improved wound dressing device with superior moisture regulation capacity for promoting wound healing is provided. The novel device of the present invention is particularly suitable for use in deeply cavitated wounds. The device is constructed of multiple matrix strands that enable the dressing to conform to individual and uniquely shaped wound areas. Furthermore, the device accelerates wound healing by displacing and allowing for the removal of excess cellular exudate and debris, thereby improving the rate of tissue repair and regeneration.

The wound dressing device of the present invention is primarily constructed of thin strands of matrix suitable for placement into the wound bed or cavity. The matrix material maybe constructed from a natural or synthetic polymer. In one embodiment, the invention is composed of polyacrylamide, wherein the acrylamide monomers are cross-linked with a cross-linking agent such as NNN'N'-methylenebisacrylamide, and incorporating a non-gellable polysaccharide and plasticizer. The matrix is constructed according to the methods and compositions as described in U.S. Pat. No. 5,196,190 to Nangia et al. which is incorporated in its entirety herein.

Natural polymers that may be used for the construction of the wound device include, but are not limited to collagen and animal hide. Synthetic polymers that may be used include, but are not limited to polyacrylate, polybuterate, polyurethane foam, silicone elastomer, rubber, nylon or vinyl.

The matrix prepared in accordance with the present invention is flexible and elastic, and may be described as a semisolid scaffold that is permeable to substances such as inorganic salts, aqueous fluids and dissolved gaseous agents including oxygen. The substances permeate the matrix through movement via intermolecular spaces among the cross-linked polymer.

The device may be constructed from one or multiple strands of matrix. When multiple strands are used in the construction, the strands are secured together by wrap, tie, glue, or alternatively by a continuous bridge of matrix between adjacent strands. Multiple strands are secured together to minimize accidental loss during removal of the dressing from the wound bed. Typically, the strands of device are bound or secured in the mid-region so that the ends of the device may float free. The advantage of free floating strands is to enable the individual strands to access a maximum area of the wound and thereby absorb the excess fluid, exudate and debris. The mechanical action of the free floating strands contributes to the trapping and removal of cellular and wound debris. Concurrently the free floating strands also conform optimally with the contours of the wound surface to maximize contact between the device and the wound bed.

Referring now to the drawings, the wound dressing device for use in the control of exudate moisture accumulation, and for stimulation of mechanical and autolytic debridement is now described.

FIG. 1 is a three dimensional view of a preferred embodiment of the wound dressing device 10 with a strand 20 of the multi-strand device with free floating strand ends 40. The strands are secured together by a bridge 30 created during the cutting stage and composed of the matrix material used to construct the device.

FIG. 2 represents a cross-section 22 of a strand 20 of the multi-strand device 10. It is intended that the cross-section 22 illustrate the sum of the linear dimensions of the sides. Preferably the sum of the linear dimensions of the sides is at least twice the numerical value of the surface area of the cross-section to provide an adequate surface area to volume ratio of the strands. More preferably, the sum of the linear dimensions of the sides is four, or more times the numerical value of the surface area of the cross section.

FIG. 3 is an illustration of the pattern of a die 45 used for cutting a preferred embodiment of the wound dressing device 10 from an appropriate matrix material. Cutting blades 55, around the perimeter of the die, release the cut-out from the stock sheet of matrix during the cutting phase of production. Within the perimeter, a series of cutting blades 57 are situated lying parallel to one another extending from the ends of the pattern toward the center but not continuing through the center so as to leave a region 50 of uncut material in the center. The pattern of blades may vary according to the purpose of the wound dressing device. For example, the patterns may vary in terms of numbers of strands 20, numbers of regions of uncut region 50 for bridging strands, and the positioning of the single or multiple bridges 50 relative to the ends of the strands. The cross section 22 of the strands may be any suitable dimension that allows the appropriate interaction between strands and wound environment. The matrix may be any non-dissolving material that is suitable for contacting the broken skin, and underlying tissues including nonabsorbent natural or synthetic materials, or absorbent natural or synthetic materials.

FIG. 4 illustrates a pattern that is an alternative pattern. It is a circular pattern for making an embodiment 80 whereby the strands 90 radiate away from a central region of uncut matrix that joins the adjacent strands in the unit.

FIG. 5 illustrates a pattern for making an embodiment whereby the bridge 95 of matrix is offset to one end of the pattern enabling the strands 100 to radiate away from the bridge in a single direction.

FIG. 6 illustrates a pattern for making an embodiment whereby the strands 120 are irregular in shape over their length from the matrix bridge 100. It is to be understood that the pattern can be any variation of these embodiments and is still within the scope of the present invention.

The matrix and multiple strands of the present invention may be coated with therapeutic agents that participate in, and improve the wound healing process. For example, the matrix and strands may include the incorporation of antimicrobial agents, including but not limited to antifungal agents, antibacterial agents, anti-viral agents and antiparasitic agents. Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin and ganciclovir.

It is to be understood that an antimicrobial agent can be incorporated into the matrix so that the agent is released over a period of time. In this way, the matrix retains its ability to kill or inhibit microorganisms over an extended period of time and thereby facilitate wound healing.

With respect to bandages and surgical gauze, the present invention is particularly useful in that various wound healing agents may be incorporated into, or coated on, the matrix to aid in the repair and regeneration of damaged tissue and prevention of infection. These agents include, but are not limited to, various growth factors such basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors α and β (TGF-α and TGF-β), interleukin-8 (IL-8); granulocytemacrophage colony stimulating factor (GM-CSF); the interleukins, and the interferons.

Other agents that may be incorporated into the matrix of the present invention are acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, and carrageenin.

Proteins that are especially useful as wound healing agents include, but not limited to, collagen, cross-linked collagen, fibronectin, laminin, elastin, and cross-linked elastin or combinations and fragments thereof.

The matrix and strands of the device may also be coated with an agent to prevent aggregation and tangling of the free floating strands. Coating agents that may be used include, but are not limited to, petrolatum, talcum, polyglycols, glycerol, propylene, glycol, vegetable oil, and animal oil.

The unique strand design of the wound dressing is particularly desirable because it enables the device to maintain its integrity and also maximize the surface area to volume ratio of its matrix. This is important since the matrix is an absorbent material where a high surface area to volume ratio increases the rate of absorption, without increasing the overall absorption capacity of the device.

The wound dressing is principally constructed of a "stranded" matrix which allows for optimal contact between the strands and the wound area. In addition, the stranded matrix construction maximizes the overall flexibility and pliability of the dressing. In embodiments of the device where multiple strands are employed, the overall flexibility and conformational characteristics of the device are maintained by binding strands in only limited and restricted areas. Minimal binding of the strands prevents the formation of rigid areas and allows for the effective and optimal utilization of numerous strands in a single device without adversely diminishing contact with the surface of the wound bed.

Another advantage of the stranded matrix construction is the "semi-porous" quality of the wound dressing that allows for the removal of extraneous cellular matter resulting during the wound healing process. The air in the inter-strands area of the device serves as a reservoir of space that may be displaced allowing for the removal of excess materials such as exudate fluid, debridement product and cellular exudate from the wound bed. As this region fills, the device may swell to provide "support" to the wound bed and surrounding tissues. A wound constitutes damaged or "missing" tissue, and when tissue is missing, the surrounding tissue may "collapse" or sag into the void. "Support" in this context therefore, means the temporary filling of the void to hold the surrounding tissue in place where it should reside.

Removal of debridement product and cellular exudate is further facilitated by unbound, loose strands of the wound dressing device. When placed upon a wound, the loose strands of the device randomly orient in the wound bed where the thin filamentous strands and free floating ends contribute to mechanical debridement of necrotic slough. Since the strands are secured and bound in at least one region, a mechanical union is formed, ensuring that all strands and necrotic tissue accumulation in the inter-strand spaces are removed from the wound when the device is changed. By contributing to the removal of extraneous wound products and cellular debris, the wound dressing device permits cleaning of the wound which in turn prevents and decreases the possibility of infection and contamination.

In one embodiment, the wound dressing device is constructed from a matrix composed of an absorbent synthetic polyacrylate material. The rate of absorption of polyacrylate is significantly increased by cutting the material into strands which increases the surface area to volume ratio. Polyacrylate material is particularly suitable for the wound dressings of the present invention because it retains its integrity during interaction with wound exudate moisture, as well as with necrotic tissue and wound debris. The wound dressing device of the present invention does not dissolve, gel or otherwise disintegrate during application to the wound. The preferred matrix swells slightly during the absorption of moisture, causing the device to conform closely with the walls of the wound bed.

In a preferred embodiment, the polyacrylate matrix is cut into free-floating strands bound together through a matrix-bridge in the mid-region. This pattern of construction imparts a significantly high surface area to volume ratio for rapid moisture movement within the absorbent matrix.

Wound dressing devices of the present invention may be produced by cutting a desired design pattern from stock sheets of matrix material. For example, the material may be die-cut from stock sheets of an absorbent polyacrylate wound dressing material. The pattern cut-out is then uniformly coated with an agent such as polyethylene glycol, polypropylene glycol or petrolatum that inhibits the free ends of the strands from sticking to one another and aids in the healing process. Following the steps of cutting and coating, the material may be sterilized using sterilization techniques known in the art such as gamma radiation, steam and heat sterilization, or chemical sterilization (such as by use of ethylene oxide).

The wound dressing devices of the present invention may be used on injured tissue and for bodily fluid drainages where control and management of fluid and secretions is desired. The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

In particular, the wound dressing device is especially applicable for usage on heavily exudating acute and chronic wounds for controlling accumulating exudate moisture, support of the wound bed and surrounding tissues. Importantly, the wound dressing is particularly effective for stimulating and supporting autolytic debridement, and therefore accelerating the wound healing process.

In use, the wound dressing device is the primary dressing placed in direct contact with the wound bed, or as near as practical against the wound bed. The device may serve as a packing material and, if required, may be secured into position with any suitable secondary wound dressing such as a wrap, tape, gauze, or pad. The dressing is a temporary wound dressing, and is not intended for permanent incorporation into the healed tissues. When necessary, the wound dressing device is changed by first removing any over-dressing material and then removing the device, whereby any accumulated necrotic tissue and exudate is lifted away. The wound dressing device of the present invention may be replaced by a fresh device or other suitable wound covering.

The device may be placed in its entirety into a wound, placed in combination with additional bundles of the same design into the wound, or cut through the bridge between strands to reduce the size or number of strands present in the wound.

The device of the present invention may be cut, shaped and modified to accomodate numerous uses and applications. For example, the device may be used as a gastric retrievable device, wherein a retrieval cord is attached to the device which is then swallowed. After absorption has taken place, the device may be retrieved and analyzed for content.

The device may undergo a swelling action as it absorbs exudate moisture, however, it will not dissolve or disintegrate. The swelling action displaces necrotic material from the wound surface and forces the material into the inter-strands regions of the device. The laden moisture content and the retention of moisture near the wound bed by the invention contributes to stimulation of the autolytic debridement process whereby the body's own enzymes break-up necrotic tissue and cellular debris. Complete removal of the device occurs due to the conjoined nature of the device.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Absorption Capacity of Polyacrylamide Matrix

It was determined that a preferred matrix material composed of cross-linked polyacrylamide and embedded natural vegetable gum absorbed approximately 7 times its weight in water. Saturation of a flat sheet of matrix material with a thickness of 0.9 mm was achieved in approximately 22 hours of continuous exposure to excess water. A similarly sized piece of flat matrix material was cut into thin strands with a calculated 200% increase in overall surface area. The total water absorption of this material was also approximately 7 times it's weight. However this material achieved saturation in approximately 5 hours. Similar comparisons were made between an intact matrix and a matrix cut in such a way as to increase the surface area between 150% and 300%. These studies revealed that the matrices retained their overall absorption capacity but there was an increased rate of absorption proportional to the increase in surface area.

EXAMPLE 2

Matrix Absorption Capacities for Various Natural Substances

Matrices, cut into strands, "test strands" were tested for absorption capacities on a variety of natural aqueous based viscous fluids. These fluids included water containing salt (0.15 M salinity), cow's whole milk, egg whites from chicken eggs, yogurt, and fetal bovine serum. The absorption of moisture by the test matrix strands ranged between 3.2 and 7.3 times the original weight of the tested devices.

EXAMPLE 3

Absorption Capacity of Matrix in Heterogeneous Biological Fluid

A polyacrylamide matrix of a preferred device, was placed into a test tube containing fetal bovine serum, in an amount equal to five times the weight of the matrix. The matrix absorbed the aqueous fluid from the serum, leaving a concentrate of serum proteins in approximately 4 hours at 4° C. The concentrated serum proteins were predominately located between the strands of the device as a thick viscous coagulation. When the device was removed from the tube, the concentrated proteins were also removed. This experiment showed that the design would assist in the debridement of the wound.

EXAMPLE 4

Construction of Stranded Matrices

Initial prototypes of the stranded matrices were prepared by taking flat sheets of polyacrylamide matrix and cutting them into thin strands using a sharp instrument such as a box knife. Several methods were tested to determine a satisfactory method for commercial production of the device. The following tests were carried out with success:

Test 4(a). Matrix material was processed through a pasta cutter using a blade for noodles.

Test 4(b). A steel rule die was constructed such that parallel bands of steel rules, separated by spacers were locked into a die block. Matrix was cut by placing the die over the matrix and press-cutting with a hydraulic press.

Test 4(c). Matrix formula was compounded and catalyzed to initiate polymerization. The matrix was then placed into a 50 ml syringe and extruded as a thin strand onto a sheet. The thin strands were allowed to complete polymerization and then were dried and cut to uniform lengths for use in the device.

Test 4(d). A rotary die was constructed with a preferred pattern. The rotary die was placed into the rotary die assembly and matrix was fed through between the rotary die and the anvil for cutting.

EXAMPLE 5

Optimization of Matrix Construction Utility

Several prototypes were constructed to optimize the utility of the device as follows:

Test 5(a) Individual strands cut from a sheet of matrix were banded together using a silicone elastimer ring. The ring, having an internal diameter of approximately 3 mm and a length of 1.5 mm, was stretched open so that between 5 to 7 strands could be threaded through and secured by the band about the middle. When placed into fluid for absorption studies, it was found that the unit nature of the device was retained throughout the absorption period and that the whole device was removed without leaving remnants in the absorption chamber.

Test 5(b) Prototypes constructed by using one strand to tie other strands together performed satisfactorily in absorption and retrieval studies.

Test 5(c) Prototypes constructed by maintaining a continuous bridge of matrix between adjacent strands were tested and shown to perform satisfactorily in absorption and retrieval studies.

It should be understood that the foregoing relates only to preferred embodiments of the present invention and that numerous modifications or alterations may be made therein without departing from the spirit and the scope of the invention as set forth in the appended claims.

What is claimed is:

1. A wound dressing device, comprising, a biocompatible polymeric material, the material being configured into multiple strands; wherein a portion of each strand is secured at a common region; and wherein at least one end of each strand is free floating.

2. The device of claim 1, wherein the biocompatible matrix comprises natural materials, or synthetic polymers or mixtures of both.

3. The device of claim 2, wherein the natural material is purified collagen or animal hide.

4. The device of claim 2, wherein the synthetic polymer is polyacrylate, polybuterate, polyurethane foam, silicone elastomer, rubber, nylon or vinyl.

5. The device of claim 1, wherein the strands are secured by a, a tie, glue, chemical bonding, closed ring or a bridge comprising continuous polymeric material.

6. A wound dressing device, comprising, a biocompatible material, wherein the material comprises a polymer network and a non-gellable polysacharide; and wherein the material is configured into multiple strands; wherein a portion of each strand is secured at a common region; and wherein at least one end of each strand is free flowing.

7. The wound dressing device of claim 1, wherein the polymeric material is cut into a rectangular shape having a central continuous portion with individual polymeric material strands extending therefrom.

8. The wound dressing device of claim 1, wherein the polymeric material is cut into a rectangular shape having a first and a second end, wherein the first end comprises a continuous portion with individual polymeric material strands extending therefrom.

9. The wound dressing device of claim 1, wherein polymeric material is cut into a circular shape having a central continuous portion, wherein individual polymeric material strands radiating therefrom.

10. The wound dressing device of claim 6, wherein the polymeric material is cut into a rectangular shape having a central continuous portion with individual polymeric material strands extending therefrom.

11. The wound dressing device of claim 6, wherein the polymeric material is cut into a rectangular shape having a first and a second end, wherein the first end comprises a continuous portion with individual polymeric material strands extending therefrom.

12. The wound dressing device of claim 1, wherein the polymeric material is cut into a circular shape having a central continuous portion, wherein individual polymeric material strands radiating therefrom.

13. The wound dressing device of claim 6, wherein the strands of the device are secured at the common region wherein the strands are secured by a tie, glue, chemical bonding, closed ring or a bridge comprising continuous polymeric material.

* * * * *